United States Patent [19]

Ishikawa et al.

[11] 4,321,273
[45] Mar. 23, 1982

[54] GERMANIUM-CONTAINING ORGANIC POLYMER AND ITS USE IN THE TREATMENT OF PULMONARY FIBROSIS

[75] Inventors: Akira Ishikawa, Tokyo; Yukihito Ishida, Fujisawa; Shiro Ikegami, Funabashi; Hiroshi Satoh, Tokyo, all of Japan; Ryuichi Sato, 2310 Kamikoizumi, Oizumicho, Ora-gun,; Gunma-ken, Japan; Setsuo Tomisawa; Shigeru Toyoshima, both of Tokyo, Japan

[73] Assignee: Ryuichi Sato, Tokyo, Japan

[21] Appl. No.: 125,947

[22] Filed: Feb. 29, 1980

Related U.S. Application Data

[62] Division of Ser. No. 12,151, Feb. 14, 1979, Pat. No. 4,271,084.

[30] Foreign Application Priority Data

Mar. 1, 1978 [JP] Japan .................................. 53-21992
Mar. 1, 1978 [JP] Japan .................................. 53-21993

[51] Int. Cl.³ ..................... A61K 31/28; A61K 31/74
[52] U.S. Cl. ........................................ 424/287; 424/78
[58] Field of Search ................................. 424/287, 78

[56] References Cited

U.S. PATENT DOCUMENTS 4,066,678  1/1978  Sato et al. ........................... 424/287

OTHER PUBLICATIONS

Chem. Abstr., 46:7925(b), 1952.
Bivlar et al., Comprehensive Inorganic Chemistry, Pergamon Press, N.Y., pp. 13 & 17 (1973).

*Primary Examiner*—Frank Cacciapaglia, Jr.
*Attorney, Agent, or Firm*—Kane, Dalsimer, Kane, Sullivan and Kurucz

[57] ABSTRACT

Germanium-containing organic polymers are obtained by polymerizing 3-trichlorogermylpropionic acid obtained by reacting halogermanium-phosphoric acid complexes with acrylic acid. The polymers are markedly effective in treating pulmonary fibrosis.

1 Claim, 4 Drawing Figures

Fibrosis (male, age: 82)

30mg/day (orally), one month two months three months

GERMANIUM-CONTAINING ORGANIC POLYMER AND ITS USE IN THE TREATMENT OF PULMONARY FIBROSIS

This is a division of application Ser. No. 12,151, filed Feb. 14, 1979, now U.S. Pat. No. 4,271,084.

BACKGROUND OF THE INVENTION

1. Field of the Invention

The present invention relates to germanium-containing organic polymers which possess important therapeutic effects as medicine.

2. Description of the Prior Art

In recent years, attention has been drawn to germanium-containing organic compounds in view of their pharmacological activities, which have been disclosed in Japanese Patent Publication No. 2964/71, Japanese Patent Application Laid Open No. 61431/73, Japanese Patent Publication Nos. 21855/71 and 2498/71, etc. The germanium-containing organic compound disclosed in these publications is a low molecular weight compound represented by the formula: $(GeOH_2CH_2COOH)_2O_3$.

SUMMARY OF THE INVENTION

As a result of extensive investigations on the synthesis of germanium-containing organic compounds other than the low molecular weight compound represented by the formula:

$$(GeCH_2CH_2COOH)_2O_3$$

drawing their attention to the pharmacological activities of the germanium-containing organic compound, the present inventors have found novel germanium-containing organic polymers and the process for the production thereof as well as their use as medicine.

The present invention is directed to a germanium-containing organic polymer represented by the formula:

$$(\equiv GeCH-CH-COZ)_n O_{1.5n} \quad \text{(III)}$$
$$\begin{array}{cc} A & B \end{array}$$

or $$(-O-\underset{|}{\overset{OH}{Ge}}-\underset{|}{\overset{A}{CH}}-\underset{|}{\overset{B}{CH}}-COZ)_n \quad \text{(IV)}$$

wherein A is a hydrogen atom, an alkyl group having 1 to 3 carbon atoms, —COOH, —COOR (wherein R is an alkyl group having 1 to 3 carbon atoms), B is a hydrogen atom or an alkyl group having 1 to 3 carbon atoms; Z is a hydroxy group, an alkoxy group having 1 to 3 carbon atoms or an alkyl group having 1 to 3 carbon atoms; n is an integer greater than 3, inclusive.

Of the germanium-containing organic polymers represented by the formulae (III) and (IV), particularly preferred are those wherein A is a hydrogen atom, a methyl group, —COOH, B is a hydrogen atom or a methyl group; and Z is a hydroxy group, a methoxy group, an ethoxy group or a methyl group.

Further the present invention is directed to a process for producing the germanium-containing organic polymer represented by the formula (III) or (IV) which comprises reacting halogermanium-phosphoric acid complexes obtained by treating germanium dioxide with hypophosphorous acid or salts thereof is hydrohalogenic acid, with a compound (I) of the formula:

$$\underset{CH=C-COZ}{\overset{A \quad B}{|\quad|}} \quad \text{(I)}$$

wherein A is a hydrogen atom, an alkyl group having 1 to 3 carbon atoms, —COOH, —COOR (wherein R is an alkyl group having 1 to 3 carbon atoms), B is a hydrogen atom or an alkyl group having 1 to 3 carbon atoms; and Z is a hydroxy group, an alkoxy group having 1 to 3 carbon atoms or an alkyl group having 1 to 3 carbon atoms; particularly preferred are in the case where A is a hydrogen atom, a methyl group, —COOH, B is a hydrogen atom or a methyl group; and Z is a hydroxy group, a methoxy group, an ethoxy group or a methyl group, and then polymerizing the resulting compound (II) represented by the formula:

$$\underset{X_3GeCH-CH-COZ}{\overset{A \quad B}{|\quad|}} \quad \text{(II)}$$

wherein A, B and Z have the same meanings as defined above, and X is a halogen atom.

DESCRIPTION OF THE PREFERRED EMBODIMENTS

Figure 1:
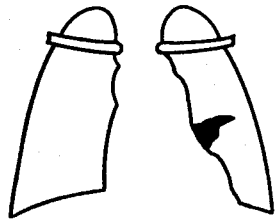
FIGS. 1–4 are a series of drawings showing the disappearance of fibrosis in a patient with senile palindromic localized pneumonia.

Representative examples for preparing the compounds of the present invention are illustratively shown below.

$$GeO_2 \xrightarrow[H_3PO_2]{HX} GeX_2 \xrightarrow{HX} HGeX_3 \rightleftarrows H^+ + GeX_3^- \quad (1)$$

or $M_2HPO_2$ (M is a metal or ammonium ions)

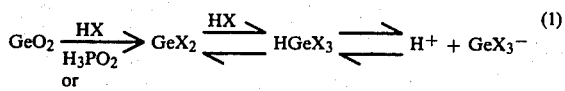

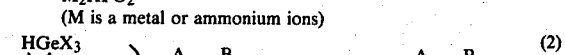

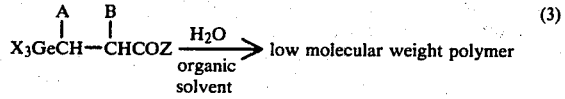

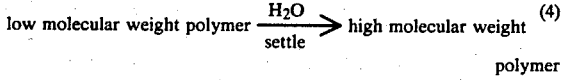

In the reaction schemes (1), (2) and (3), A, B, X and Z have the same meanings as defined above, and the low molecular weight polymer and the high molecular weight polymer shown in the reaction schemes (3) and (4) are germanium-containing organic polymers represented by the formulae (III) and (IV) which are objective compounds of the present invention. Whether the objective compound is of high molecular weight polymer or of low molecular weight polymer is determined by the number of n, more simply, depending upon the solubility of the compound in water.

Based upon the reaction schemes (1), (2), (3) and (4) described above, the process for producing the compounds of the present invention is described below in detail.

Germanium dioxide is reduced with hypophosphorous acid or salts thereof (metal salts or ammonium salts are preferred), whereby the germanium atom becomes di-valent and germanium dihalide is formed. The germanium dihalide is in equilibrium with germanium hydrogen trihalide wherein the germanium atom takes tetra-valence, in hydrohalogenic acid. It is believed that this germanium hydrogen trihalide would be in equilibrium with the dissociation form shown at the right end of the reaction scheme (1), in an aqueous solution (see reaction scheme (1) ). It is likely that phosphoric acid would contribute to this equilibrium system, since this reaction solution is diluted with water to thereby isolate a halogermanium-phosphoric acid complex.

To the thus formed germanium reagent, a polarized unsaturated compound, i.e., a compound represented by the formula:

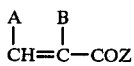

$$\overset{A}{\underset{CH=C-COZ}{|}} \overset{B}{|} \quad (I)$$

wherein A, B and Z have the same meanings as defined above, is added, then a white crystalline compound represented by the formula:

$$\overset{A}{\underset{X_3GeCH-CHCOZ}{|}} \overset{B}{|} \quad (II)$$

wherein A, B, X and Z have the same meanings as defined above, is formed in high yield (see the reaction scheme (2) ). As described above, the halogermanium-phosphoric acid complex obtained in accordance with the reaction scheme (1) can be stably isolated and, accordingly, this complex can previously be prepared according to the reaction scheme (1), followed by isolation. When it is desired to proceed with the reaction of the reaction scheme (2), this complex is added to an organic solvent or water and the resulting mixture is treated with hydrogen halide. The resulting solution is reacted with the compound of the formula (I) to obtain the compound of the formula (II), alternatively.

The compound represented by the formula (II) is dissolved in acetone or other organic solvents miscible with water (e.g. ethanol, methanol, cellosolve, acetonitrile, tetrahydrofuran, dioxane, dimethoxyethane, digline, dimethylsulfoxide, dimethylformamide) and then water is added to the resulting solution to obtain a low molecular weight polymer which is one of the compounds of the present invention (see the reaction scheme (3) ). In the reaction of the reaction scheme (3), in the case where organic solvents immiscible with water are employed in place of solvents miscible with water, the low molecular weight polymer is obtained by mixing and agitating with water. This low molecular weight polymer is relatively easily soluble in water.

When the water soluble low molecular weight polymer is suspended in a small amount of water and the suspension is allowed to settle, the high molecular weight polymer which is another objective compound of the present invention is obtained (see the reaction scheme (4)). This high molecular weight polymer is sparingly soluble in water and differs from the low molecular weight polymer in its crystalline form.

Both the low molecular weight polymer and the high molecular weight polymer are compounds of the present invention, and are represented by the formula:

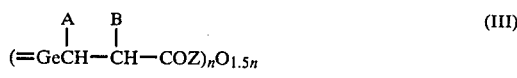

$$(=GeCH-CH-COZ)_n O_{1.5n} \quad (III)$$

or

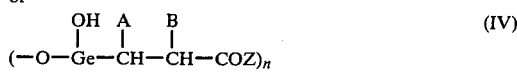

$$(-O-Ge-CH-CH-COZ)_n \quad (IV)$$

with OH, A, B substituents wherein A, B, Z and n are the same as defined above. Determination of either the low molecular weight polymer or the high molecular weight polymer can be made by the number of n in the formulae above, more simply, depending upon the solubility in water.

It has been made apparent from the infrared absorption spectrum, x-ray diffraction spectrum of powders, and the like that the compounds in accordance with the present invention are novel compounds different from heretofore known compound:

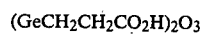

$$(GeCH_2CH_2CO_2H)_2O_3$$

The compounds of the present invention possess important therapeutic effects and exhibit marked effects in use for treating a variety of abnormal physiological symptoms as shown below.

The compounds of the present invention are administered through administration routes such as oral administration, intraveneous administration, subcutaneous administration, intramuscular administration, intrarectal administration, and the like.

These compounds are also used on the skin in a direct form such as ointment.

In the case of oral administration, a sufficient effect is achieved in the daily dose of 0.1 mg/kg/day to 150 mg/kg/day. A sufficient effect is also achieved in the daily dose of 0.02 mg/kg/day to 20 mg/kg/day in intravenous injection, and in the daily dose of 0.04 mg/kg/day to 30 mg/kg/day in subcutaneous as well as intramuscular injections. For rectal use and as ointment, a pharmaceutical preparation which comprises mixing the active ingredient with a variety of bases in a ratio of 0.1 to 5% is obtained.

EXAMPLE OF THE TREATMENT OF FIBROSIS

Markedly effective examples are noted in senile palindromic localized pneumonia. Capability of the compounds of the present invention in the retrogression of fibrosis is conspicuous.

Figure 2:
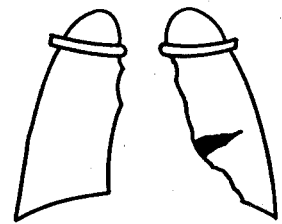
Figure 3:
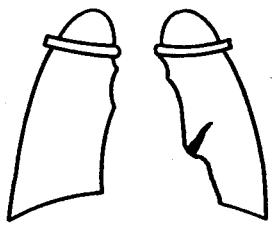
Figure 4:
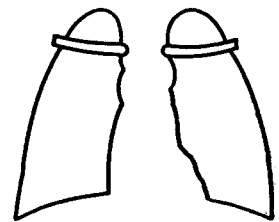

In FIG. 1–4, mammograms are illustratively shown; FIG. 1 is before administration of the low molecular weight polymer (A); the mammogram FIG. 2 is one month after the medication; FIG. 3 is two months after and (d) is three months after; per os at the dose of 30 mg/day. In FIG. 2 and FIG. 3, a tendency of complete retrogression of fibrosis was noted. Fibrosis completely retrogressed in FIG. 4.

Preparation of the compounds of the present invention will be described in detail with reference to the examples below.

EXAMPLE 1

Preparation of 3-trichlorogermylpropionic acid from germanium dioxide

In 600 ml. of conc. hydrochloric acid was suspended 104.6 g. (1 mol) of germanium dioxide. To the resulting suspension was added 160 ml. (1 mol as the minimum titer) of 50% hypophosphorous acid solution while stirring. The reaction mixture was heated under reflux for about 3 hrs. while stirring to become a transparent solution, all being dissolved therein. With the addition of 72 g. (1 mol) of acrylic acid to the solution under agitation heat generated. Since the reaction was exothermic, the whole amount of acrylic acid was added at such a rate that the reaction temperature did not exceed 50° C. When almost a half amount of acrylic acid was dropwise added, crystals were deposited from the reaction solution by adding a seed for crystallization, etc., which was advantageous. After adding the whole amount of acrylic acid, stirring was continued for further 0.5 to 1 hr. After cooling, the crystals were taken by suction-filtration, followed by drying under reduced pressure. Alternatively, wet crystals were dissolved in ether, methylene chloride, chloroform, benzene, etc. Thereafter, the solution was dried over a drying agent such as $MgSO_4$, etc. and the solvent was distilled off to obtain the crystals. As such, 227 g. (90% in yield) of white crystals were obtained. By recrystallization from n-hexane, white needles were obtained. The melting point thereof was 83.5°–86° C. which was identical with that in the literature. Also, elemental analysis, infrared absorption spectrum and NMR spectrum supported the structure of 3-trichlorogermylpropionic acid.

In addition, also in the case where metal salts or ammonium salts of hypophosphorous acid were employed in lieu of hypophosphorous acid, 3-trichlorogermylpropionic acid was similarly obtained.

Further, also in the case where other unsaturated compounds represented by the formula (I) were employed in lieu of acrylic acid, the corresponding compounds represented by the formula (II) were obtained as shown in the table below.

| Starting Material (Compound of the formula (I)) | Product (Compound of the formula (II)) | Yield (%) |
|---|---|---|
| $CH_2=CHCOOC_2H_5$ | $Cl_3GeCH_2CH_2COOC_2H_5$ | 70 |
| $CH_2=\overset{\underset{\mid}{CH_3}}{C}COOH$ | $Cl_3GeCH_2\overset{\underset{\mid}{CH_3}}{C}HCOOH$ | 79 |
| $HOOCCH=CHCOOH$ | $Cl_3GeCHCH_2COOH$ with $COOH$ | 68 |
| $CH_3CH=CHCOOH$ | $Cl_3GeCHCH_2COOH$ with $CH_3$ | 88 |
| $CH_2=CHCOCH_3$ | $Cl_3GeCH_2CH_2COCH_3$ | 60 |

EXAMPLE 2

Preparation of a low molecular weight polymer (A) of 3-oxygermylpropionic acid

In 1.3 l. of acetone, a solvent compatible with water, was dissolved 252 g. (1 mol) of 3-trichlorogermylpropionic acid. To the solution, 1.3 l. of water was added with stirring. White hairy crystals were precipitated out. The reaction liquid was allowed to stand overnight. Then, crystals were collected by suction-filtration. The so obtained crystals were washed with acetone sufficiently, followed by drying under reduced pressure. White needle-like low molecular weight polymer (A) was obtained in an amount of 144 g. (85% in yield). In addition, also in the case where other solvents which are miscible with water (e.g., ethanol, methanol, cellosolve, acetonitrile, tetrahydrofuran, dioxane, dimethoxyethane, diglime, dimethylsulfoxide, dimethylformamide, etc.) are employed in place of acetone, the low molecular weight polymer (A) can also be obtained likewise. Furthermore, the low molecular weight polymer (A) can also be obtained using solvents which are immiscible with water (e.g., chloroform, methylenechloride, carbon tetrachloride, benzene, ether, etc.). In this case, the low molecular weight polymer (A) was precipitated out when a solution of 3-trichlorogermylpropionic acid was throughly shaked with water. Crystals of this low molecular weight polymer (A) neither decompose nor melt at temperatures below 320° C. It is found that the polymer differs from the germanium-containing organic compound prepared in accordance with the method described in Japanese Patent Publication No. 2964/71 since infrared absorption spectrum and x-ray diffraction spectrum of powders are completely different. In addition, the low molecular weight polymer (A) was relatively easily soluble in water and the solubility in water was about 1 g./100 ml. (25° C.).

EXAMPLE 3

Preparation of high molecular weight polymer (B) of 3-oxygermylpropionic acid

A suspension of 40 g. of the polymer (A) in 400 ml. of water was settled at room temperature until all needles were changed to heavy bright prisms (it required for 1–3 weeks). After suction, the crystals were taken by filtration and dried under reduced pressure. Thus, 33 g. of white prism high molecular weight polymer (B) which was insoluble in water was obtained. This polymer did not decompose or melt at temperatures below 320° C. and its powder x-ray diffraction spectrum as well as infrared absorption spectrum were different from those of the low molecular weight polymer (A). Accordingly, the structure of the polymer (B) was different from that of the polymer (A).

EXAMPLE 4

Isolation of germanium chloride-phosphoric acid complex

As shown in Example 1, a solution obtained by the reaction of germanium dioxide and hypophosphorous acid in conc. hydrochloric acid was poured into 3 l. of cold water while shaking, whereby a white solid germanium chloride-phosphoric acid complex was precipitated out. By suction-filtration, the solid was collected, washed with acetone and then dried under reduced pressure. It is recommended to avoid water-washing since the solid is colored when washed with water.

From 1 mol. (104.6 g.) of germanium dioxide, 136 g. of the complex was obtained. It is assumed that the complex would be a complex of chlorogermanium ($Ge^{II}$ or $Ge^{IV}$) and phosphoric acid. The complex is an effective reagent for synthesis of germanium-containing organic compounds.

EXAMPLE 5

Another preparation of organic trichlorogermyl compound from germanium chloride-phosphoric acid complex The complex isolated in Example 4 was suspended in a solvent such as ethanol, methanol, dichloromethane, chloroform, carbon tetrachloride, ether, or the like. The suspension was saturated under ice cooling by blowing dry hydrogen chloride thereinto. When water was employed, conc. hydrochloric acid was used. The complex gradually disappeared at the same time when hydrogen chloride was blown in the system and a completely transparent solution was formed depending upon solvent. The unsaturated compound represented by the formula (I) was added to the system in an equimolar amount. The mixture was warmed (40°–60° C.) for 1 hr. After post-treatment, the corresponding organic trichlorogermyl compound of the formula (II) was obtained.

In the case of the unsaturated compound (I) to which hydrogen chloride was easily added, the aforementioned treated solution of the complex was provided for use after previously heating the solution at 40°–60° C. for 1 hr. and removing an excess of hydrogen chloride from the system. The corresponding organic trichlorogermyl compounds (II) were thus obtained as shown in the table below.

| Starting Material (Compound of the formula (I)) | Product (Compound of the formula (II)) | Yield (%) |
| --- | --- | --- |
| $CH_2{=}CHCOOH$ | $Cl_3GeCH_2CH_2COOH$ | 80 |
| $CH_2{=}CHCOOC_2H_5$ | $Cl_3GeCH_2CH_2COOC_2H_5$ | 58 |

EXAMPLE 6

Preparation of trichlorogermyl organic acid ester

Of a variety of organic trichlorogermyl compounds obtained in Examples 1 and 5, the trichlorogermyl organic acids were esterified.

Esters could be obtained by dissolving various trichlorogermyl organic acids into a solvent such as methanol, ethanol, or the like, saturated with hydrogen chloride, and then reacting at temperatures of 0°–60° C. for 2–3 hrs. For example, ethyl-3-trichlorogermyl propionate was obtained in yield of 90% by treating as described above (b.p. 94° C./5 mmHg).

EXAMPLE 7

The organic trichlorogermyl compound shown in the middle column of the table of Example 1, the organic trichlorogermyl compound shown in the middle column of the table in Example 5 and the trichlorogermyl organic acid ester obtained in accordance with Example 6 were treated according to Examples 2 and 3. Thus, the corresponding low molecular weight polymer and high molecular weight polymer were obtained.

What is claimed is:

1. A method of treating an animal suffering from pulmonary fibrosis, which comprises; administering to said animal an effective amount to relieve said suffering of a polymer selected from those of the formulae:

and

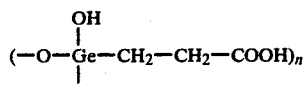

wherein n is an integer greater than 3, inclusive.

* * * * *